United States Patent [19]
Inagi et al.

[11] Patent Number: 5,773,028
[45] Date of Patent: Jun. 30, 1998

[54] HYDROPHILIC ADHESIVE BASE MATERIAL

[75] Inventors: Toshio Inagi, Mishima; Makoto Kanebako, Fuji, both of Japan

[73] Assignee: Kowa Co., Ltd., Nagoya, Japan

[21] Appl. No.: 671,541

[22] Filed: Jun. 27, 1996

[30] Foreign Application Priority Data

Jul. 4, 1995 [JP] Japan .................................. 7-168384

[51] Int. Cl.[6] ........................... A61K 47/32; A61L 15/58
[52] U.S. Cl. ......................... 424/487; 524/503; 528/481
[58] Field of Search ................................. 424/78.08, 487

[56] References Cited

U.S. PATENT DOCUMENTS

| | | | |
|---|---|---|---|
| 5,164,492 | 11/1992 | Kitazawa et al. ...................... | 536/116 |
| 5,173,554 | 12/1992 | Kitazawa et al. ...................... | 526/258.2 |
| 5,288,403 | 2/1994 | Ohno ...................................... | 210/508 |
| 5,646,221 | 7/1997 | Inagi et al. ......................... | 526/238.23 |

Primary Examiner—Peter F. Kulkosky
Attorney, Agent, or Firm—Oblon, Spivak, McClelland, Maier & Neustadt, P.C.

[57] ABSTRACT

Described is a hydrophilic adhesive base material comprising a hydrophilic crosslinked polymer obtained by polymerizing (A) (a) a glucosyloxyalkyl (meth)acrylate, (b) an alkyl (meth)acrylate and/or a hydroxyalkyl (meth)acrylate and (c) a polyfunctional monomer; and (B) polyvinyl alcohol. The hydrophilic adhesive base material according to the present invention is free from lowering in the water content and has excellent mechanical strength and adhesion to the skin so that it is useful as adhesive layers in plasters, various medical pads and also medicament-impregnated dermatologic medicines.

10 Claims, 8 Drawing Sheets

HYDROPHILIC ADHESIVE BASE MATERIAL

BACKGROUND OF THE INVENTION

1. Field of the Invention

This invention relates to a hydrophilic adhesive base material which has excellent mechanical strength and adhesion to the skin and is useful as plasters, medical pads, dermatologic medicines and the like.

2. Description of the Related Art

For heightening of percutaneous absorption, numerous researches have heretofore been made on adhesive pad base materials impregnated with a water-soluble medicament. For example, a polyacrylamide gel (Okabe K. et al., J. Control Rel., 4, 318(1986)), a gel obtained by adding a polyvalent metal salt to polyacrylic acid and a salt thereof (Japanese Patent Laid-Open No. 167117/1991), a gel composed of a sulfonic-acid-containing monomer (Japanese Patent Laid-Open No. 91021/1992) and the like are known. The above-mentioned gels are however accompanied with the problem that because many of the water-soluble medicaments are dissociating in the water solution and peptides, proteins or the like are charged with a cation or anion at pHs other than an isoelectric point, a functional group existing in the dissociated form in the above base materials form an ion bond with the dissociated medicament, thereby inhibiting the transfer of the medicament to the skin.

On the other hand, an agar gel (Makoto Haga, et al., Summaries of the 112-th Lecture of the Japan Pharmacological Society, 4, 52(1992)), a hydroxypropylmethyl cellulose gel (Riviere J. E. et al., J. Pharm. Sci., 81(6), 504(1992)), a poly(2-hydroxyethyl methacrylate) gel (Banga A. K. et al., Pharm. Res., 10(5), 697(1993)), and a gel obtained by incorporating a plasticizer in polyglucosyloxyethyl (meth)acrylate or polyglucosyloxypropyl (meth)acrylate (Japanese Patent Laid-Open No. 193057/1991) are accompanied with the problem that although they are nonionic, they have weak adhesion to the skin.

A gel obtained by incorporating a highly water-absorptive resin or a hydrophilic polymer in polyvinyl alcohol (Japanese Patent Laid-Open No. 230313/1993) is also known. It is however accompanied with the problem that it has weak mechanical strength in spite of having adhesion so that forming of gel cannot be effected easily. With a view to improving the mechanical strength, it has been attempted to increase the crosslinking density of the gel by adding a condensation agent such as glutaraldehyde or the like or exposing it to radiation. These attempts make it possible to improve the mechanical strength, but at the same time lower the water content and adhesion and cause a problem in absorption and the like.

For the improvement of the mechanical strength without lowering the water content, there has been attempts to freeze a concentrated water solution of polyvinyl alcohol at low temperature for a short time and then to thaw the frozen solution (hereinafter abbreviated as "freeze-thaw method") or alternatively to conduct freezing at low temperature for a short time and then to dry without thawing (which will hereinafter be called "freeze-dry method").

When the freeze-thaw method is applied, gel is not formed by single freezing. An increase in the freezing frequency on the other hand heightens the gelation degree but markedly deteriorates the mechanical strength so that it is difficult to use the gel formed by the freeze-thaw method as an adhesive. The freeze-dry method is on the other hand accompanied with the problem that it lowers the water content in the gel.

An object of the present invention is to provide an adhesive base material having excellent mechanical strength and adhesion to the skin without lowering the water content.

Under the foregoing circumstances, the present inventors have carried out an extensive investigation. As a result, it has been found that a hydrophilic adhesive base material which contains a specific hydrophilic crosslinked polymer and polyvinyl alcohol has excellent mechanical strength and adhesion to the skin without a reduction in the water content, leading to the completion of the present invention.

In one aspect of the present invention, there is thus provided a hydrophilic adhesive base material comprising:

(A) a hydrophilic crosslinked polymer obtained by polymerizing (a) a glucosyloxyalkyl (meth)acrylate, (b) an alkyl (meth)acrylate and/or hydroxyalkyl (meth)acrylate, and (c) a polyfunctional monomer; and (B) polyvinyl alcohol.

In another aspect of this invention, there is also provided a dermatologic medicine composition comprising the hydrophilic adhesive base material and a medicament.

The hydrophilic adhesive base material according to the present invention has good swelling property, can swell uniformly, is free from a reduction in the water content, and has excellent mechanical strength and adhesion to the skin, so that it is useful as adhesive layers in plasters, various medical pads and medicament-impregnated dermatologic medicines.

DETAILED DESCRIPTION OF THE PREFERRED EMBODIMENTS

Figure 1A:
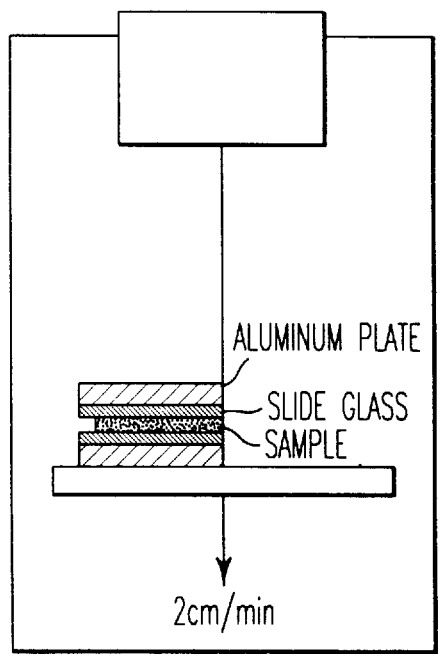
FIG. 1 depicts the construction of an apparatus used for the measurement of adhesion in Test 1.

The hydrophilic crosslinked polymer, which is the component (A), used in the present invention is obtained by polymerizing the components (a), (b) and (c).

Examples of the glucosyloxyalkyl (meth)acrylate (a) usable herein include those represented by the following formula (1):

(1)

wherein R represents a hydrogen atom or a methyl group, G—O— represents a saccharide residual group having no protecting group, and n stands for 2 or 3.

Preferred examples of the saccharide residual group (glucosyloxy group) represented by G—O— in the formula (1) include monosaccharides and oligosaccharides having 1 to 10 saccharide units, with those having 1 to 5 saccharide units being particularly preferred. Specific examples of the monosaccharides include hexoses such as glucose, mannose, galactose, glucosamine, mannosamine and galactosamine; and pentoses such as arabinose, xylose and ribose. Specific examples of the oligosaccharides, on the other hand, include disaccharides such as maltose, lactose, trehalose, cellobiose, isomaltose, gentiobiose, melibiose, laminaribiose, chitobiose, xylobiose, mannobiose and sophorose; maltotriose; isomaltotriose; maltotetraose; maltopentose; mannotriose; manninotriose; and hydrolyzates of starch, cellulose, chitin, chitosan and mannan, such as dextrin listed in the Pharmacopoeia of Japan, achrodextrin, British gum and cellodextrin.

In the formula (1), a methyl group and 2 are preferred as R and n, respectively.

Particularly preferred examples of the glucosyloxyalkyl (meth)acrylate include 2-glucosyloxyethyl methacrylate, 2-mannosyloxyethyl methacrylate and 2-galactosyloxyethyl methacrylate.

Concerning the component (b), illustrative of the alkyl (meth)acrylate include $C_{1-24}$ alkyl (meth)acrylates such as methyl meth(acrylate), ethyl (meth)acrylate, n-butyl (meth)acrylate, isobutyl (meth)acrylate, hexyl (meth)acrylate, octyl (meth)acrylate, 2-ethylhexyl (meth)acrylate, isooctyl (meth)acrylate, decyl (meth)acrylate, isodecyl (meth) acrylate, lauryl (meth)acrylate and stearyl (meth)acrylate. Of these, particularly preferred are methyl (meth)acrylate and n-butyl (meth)acrylate, because they impart the gel with better forming property.

Concerning the component (b), examples of the hydroxyalkyl (meth)acrylate include $C_{1-8}$ hydroxyalkyl (meth) acrylates such as 2-hydroxyethyl (meth)acrylate and hydroxypropyl (meth)acrylate. Of these, 2-hydroxyethyl methacrylate is particularly preferred from the viewpoints of the safety to the body and the like.

It is preferred to mix the glucosyloxyalkyl (meth)acrylate (a) and the alkyl (meth)acrylate and/or the hydroxyalkyl (meth)acrylate (b) at a molar ratio of 10:0.1 to 10:10, particularly 10:1.5 to 10:10. In particular, when methyl (meth)acrylate is employed as the component (b), the molar ratio of 10:0.1 to 10:10 is preferred, while when n-butyl (meth)acrylate is employed, the molar ratio of 10:0.5 to 10:2 is preferred. Alternatively, when 2-hydroxyethyl methacrylate is used, that of 10:0.5 to 10:1 is preferred. As the component (b), it is possible to use the alkyl (meth)acrylates and hydroxyalkyl (meth)acrylates either singly or in combination.

As the polyfunctional monomer (c), any monomer can be used insofar as it has at least two functional groups per molecule. Examples include monomers having at least two vinyl groups per molecule such as N,N'-methylenebisacrylamide, ethylene glycol di(meth)acrylate, diethylene glycol di(meth)acrylate, triethylene glycol di(meth)acrylate, polyethylene glycol di(meth)acrylate, propylene glycol di(meth)acrylate, polypropylene glycol di(meth)acrylate, 1,4-butylene glycol di(meth)acrylate, 1,6-hexanediol di(meth)acrylate and 1,10-decanediol di(meth) acrylate; and monomers having at least two allyl groups per molecule such as diallyl phthalate, diallyl maleate, diallyl adipate, triallyl isocyanate and diethylene glycol bisallylcarbonate. Of these, particularly preferred is N,N'-methylenebisacrylamide.

The preferred molar ratio of the polyfunctional monomer (c) to the sum of the glucosyloxyalkyl (meth)acrylate (a) and alkyl (meth)acrylate and/or hydroxyalkyl (meth)acrylate (b) falls within a range of from 1:100 to 1:3200, with a range of from 1:200 to 1:800 being particularly preferred. The smaller the molar ratio of the polyfunctional monomer, the higher the swelling rate but the lower the mechanical strength. At the molar ratios exceeding the above range, on the other hand, gel is formed but becomes fragile and tends to lose its appearance. A molar ratio within the above range is therefore preferred.

The hydrophilic crosslinked polymer used in the present invention can also be obtained by additionally polymerizing one or more monomers other than the above monomers (a) through (c). Illustrative of such additional monomers include carboxyl-containing, amido-containing and amino-containing monomers. Examples of the carboxyl-containing monomers include unsaturated carboxylic acids such as (meth)acrylic acid, maleic acid, fumaric acid and crotonic acid; examples of amido-containing monomers include (meth)acrylamide, dimethyl(meth)acrylamide, diethyl (meth)acrylamide, butoxymethyl(meth)acrylamide, ethoxyethyl (meth)acrylamide, diacetone (meth)acrylamide and vinylpyrrolidone; and examples of amino-containing monomers include dimethylamino(meth)acrylate and diethylamino(meth)acrylate. Further examples include vinyl acetate, styrene, vinyl chloride, acrylonitrile, ethylene, propylene and butadiene.

No particular limitation is imposed on the polymerization process. The polymerization of the glucosyloxyalkyl (meth) acrylate (a), the alkyl (meth)acrylate and/or hydroxyalkyl (meth)acrylate (b), and the polyfunctional monomer (c) may therefore be conducted in a manner known per se in the art.

No particular limitation is imposed on the method of radical polymerization. Any one of bulk polymerization, solution polymerization, suspension polymerization and emulsion polymerization can be employed. In addition, no particular limitation is imposed on a polymerization initiator suitable for use in the radical polymerization. A suitable polymerization initiator can be selected depending on the monomers, a reaction solvent and the like. When a water-soluble monomer or, as a reaction solvent, water or a water-containing solvent is employed, usable examples of the polymerization initiator include hydrochlorides of an azo compound such as 2,2'-azobis(2-aminodipropane)-dihydrochloride and persulfates such as ammonium persulfate and potassium persulfate. When a hydrophobic monomer or, as a reaction solvent, an organic solvent is employed, usable examples of the polymerization initiator include t-butyl peroctanoate; peroxides such as benzoyl peroxide, di-tert-butyl peroxide and acetyl peroxide; and azo compounds such as 2,2'-azobisisobutylonitrile, 2,2'-azobis(2-methylbutylonitrile), 2,2'-azobis(2,4-dimethylvaleronitrile) and dimethyl2,2'-azobis(2-methylpropionate).

It is desired to add the polymerization initiator in an amount of 0.01 to 10 wt. % based on the sum of the monomers.

Examples of the solvent suitable for use in conducting the polymerization by solution polymerization include water, methanol, isopropyl alcohol, dioxane, tetrahydrofuran, acetone, acetonitrile, dimethyl formamide, dimethyl sulfoxide and N-methylpyrrolidone. These solvents can be used either singly or in combination.

When a conventional radical polymerization initiator is used, for example, it is preferred to conduct the polymerization reaction at 40°–80° C. for 2–72 hours. To increase the polymerization degree by decomposing the polymerization initiator, it is preferred to conduct the polymerization reaction for a predetermined time and then to proceed further with the polymerization reaction at an elevated temperature.

Alternatively, it is also possible to conduct the polymerization without using any polymerization initiator. This can be effected by exposing the monomers to radiation, light, ultraviolet rays or low-temperature plasma to form polymerization-initiating free radicals and then performing the polymerization. Examples of the radiation usable here include high-energy ionizing radiation such as α-rays, β-rays, γ-rays, accelerated electrons and X-rays. Of these, γ-rays and accelerated electrons are preferred. Exposure to light or ultraviolet rays can generally be conducted using a mercury lamp, with the exposure through a filter at a wavelength of at least 300 nm being preferred. Preferred examples of the low-temperature plasma include those obtained by a glow discharge or a corona discharge. It is desired to add an oxygen scavenger upon such polymerization.

Exclusion of the polymerization initiator makes it possible to avoid the toxicity of the polymerization initiator.

Of hydrophilic crosslinked polymers available by conducting polymerization reactions as described above, the polymer obtained by polymerizing 2-glucosyloxyethyl (meth)acrylate, methyl (meth)acrylate and N,N'-methylenebisacrylamide is particularly preferred.

The forming property and adhesion of the gel can be enhanced when the hydrophilic crosslinked polymer so obtained is used in a pulverized form, although it can also be used as is or in the form of a plate. The pulverization makes it possible to impregnate the polymer uniformly with the solvent and further, to enlarge the surface area of the polymer per unit weight, thereby increasing its swelling speed and swelling degree. In the present invention, the preferred particle size of the pulverized polymer falls within a range of from 200 mesh to 50 mesh.

It is preferred that as a water absorption rate, the weight of the hydrophilic crosslinked polymer (A) after absorbing water is 4–40 times, particularly 6–20 times as much as the original weight. Within this range, the polymer uniformly swells in an aqueous solution of polyvinyl alcohol and excellent mechanical strength can be attained. To heighten the water absorption rate, it is only necessary to lower the crosslink density or to use a crosslinker of a longer chain length. The crosslink density or the chain length of the crosslinker can be selected as desired to an extent not impairing the mechanical strength of the polymer. In addition, it is desired to determine the water absorption rate at need according to the application or the like of the adhesive base material of the present invention.

Incidentally, the water absorption rate of the hydrophilic crosslinked polymer can be indicated by a swelling rate which can be determined by the formula described below. For example, when the weight after water absorption becomes 4 times as much as the original weight, the swelling rate becomes 300%. It is preferred that the swelling rate of the hydrophilic crosslinked polymer (A) when immersed in water is 300–3900%, particularly 500 to 1900%.

$$\text{Swelling rate (\%)} = \frac{W - W_o}{W_o} \times 100 \quad (1)$$

$W_o$ = Dry Initial weight $W$ = Weight upon saturated swelling

The polymer swelled by the impregnation with a solvent preferably has peel strength of 20 g/cm² or greater when measured relative to glass. Peel strength of 25 g g/cm² or greater is particularly preferred because excellent adhesion to the skin can be obtained.

The peel strength can be determined by the following formula:

$$\text{Peel strength (g/cm}^2\text{)} = \frac{W_D}{A} \quad (2)$$

$W_D$ : Load upon peeling $A$ : Cross section area of sample

It is necessary to polymerize the above-described three components, (a), (b) and (c) to obtain the hydrophilic crosslinked polymer (A). When the (meth)acrylate copolymer not containing the component (a) is employed, a sufficient mechanical strength cannot be obtained without lowering the water content and it becomes impossible to conduct the forming of the gel.

As the polyvinyl alcohol (B) suitable for use in the present invention, that having a saponification degree of 95 mole% or higher, particularly 98 mole% or higher is preferred. In addition that having an average polymerization degree of 1,000 to 3,000, particularly 1,700 to 2,400, is preferred.

The hydrophilic adhesive base material according to the present invention can be prepared, for example, by the freeze-thaw method by mixing a hydrophilic crosslinked polymer with an aqueous solution of polyvinyl alcohol, freezing the resulting mixture and then thawing. Described specifically, the hydrophilic adhesive base material according to the present invention can be prepared by spreading an aqueous solution containing the components (A) and (B) to a desired area between sheets of a tack-free resin such as silicone, Teflon or the like or rubber with a spacer of a desired thickness interposed therein, hermetically sealing and allowing it to stand at a low temperature lower than a room temperature and thereby freezing, followed by thawing. It is preferred that the freezing is conducted at 5° C. or lower for 1 hour or more, with −10° C. or lower and 10 hours or more being particularly preferred. It is desired to conduct thawing at room temperature or lower, with about 5° C. being particularly preferred. It is preferred that the freeze-thaw procedure is conducted 1–5 times, with 2–4 times being particularly preferred.

In this case, it is preferred to dissolve polyvinyl alcohol (B) in water to give a concentration of 3–10 wt. % (w/w%), with 4–7 wt. % (w/w%) being particularly preferred. In addition, it is preferred to mix the component (A) in such an aqueous solution of polyvinyl alcohol to give a concentration of 15–50 wt. % (w/w%), with 15–30 wt. % (w/w%) being particularly preferred.

The hydrophilic adhesive base material according to the present invention can be prepared as described above by the freeze-thaw method using an aqueous solution of polyvinyl alcohol. It is also possible to add a hydrophilic polymer to the above aqueous solution, thereby improving the forming property and adhesion of the resulting base material.

Examples of the hydrophilic polymer usable here include cellulose derivatives such as methyl cellulose, hydroxypropyl cellulose, hydroxypropylmethyl cellulose and hydroxyethyl cellulose; starch derivatives such as dextrin, α-cyclodextrin and pullulan; synthetic polymers such as polyvinyl pyrrolidine and carboxyvinyl polymer; and natural polymers such as gum arabic, sodium hyaluronate, sodium alginate, propylene glycol alginate, agar, gelatin, lactose, sucrose and xanthan gum.

These hydrophilic polymers can be used either singly or in combination. It is desired to add it (them) to the aqueous solution of polyvinyl alcohol to give a concentration of 0–10 wt. % (w/w%), particularly 0.25–5 wt. % (w/w%).

In a similar manner to the addition of the hydrophilic polymer, it is possible to add an antiseptic. Examples of such an antiseptic include sodium azide, aminoethylsulfonic acid, benzoic acid, sodium benzoate, benzyl benzoate, sodium edetate, cetyl pyridinium chloride, benzalkonium chloride, benzethonium chloride, anhydrous sodium sulfate, isobutyl paraoxybenzoate, isopropyl paraoxybenzoate, ethyl paraoxybenzoate, butyl paraoxybenzoate, propyl paraoxybenzoate and methyl paraoxybenzoate.

These antiseptics can be used either singly or in combination. It is desired to add it (them) to the aqueous solution of polyvinyl alcohol to give a concentration of 0.001–10 wt. % (w/w%), with 0.01–5 wt. % (w/w%) being particularly preferred.

The adhesive base material according to the present invention can also be used in a form deposited on a commercially-available support. Illustrative usable examples include plastic sheets made of polyethylene, polypropylene, an ethylene-vinyl acetate copolymer, vinylon, a polyester, polyurethane, nylon or the like; nonwoven fabrics made of rayon, a polyester or the like; and woven fabrics made of a polyester, an acrylic resin, silk, cotton or the like.

The hydrophilic adhesive base material according to the present invention can be applied as a dermatologic medicine composition by dissolving a medicament in its aqueous solution, thereby improving the percutaneous absorption of the medicament. Examples of the medicament usable here include protein and peptide preparations, antipyretic, antiphlogistic and analgesic agents, steroidal antiinflammatory agents, vasodilators, antihypertensive and antiarrhythmic agents, hypotensive agents, antitussive expectorants, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents and dysuric agents.

Examples of the protein and peptide preparations include insulin, calcitonin, elcatonin, vasopressin, batroxobin, gonadorelin acetate, octreotide acetate, desmopressin acetate, nafarelin acetate, buserelin acetate, leuprorelin acetate, calcitonin salmon, somatropin, hyaluronidase, protirellin, angiotensin II and arginine-vasopressin.

Specific examples of the antipyretic, antiphlogistic and analgesic agents include indomethacin, salicylic acid, aspirin, acetaminophen, sodium dichlofenac, ibuprofen, sulindac, naproxen, ketoprofen, flufenamic acid, ibufenac, fenbufen, alclofenac, phenylbutazone, mefenamic acid, bendazac, piroxicam, flurbiprofen, pentazocine, buprenorphine hydrochloride, butorphanol tartrate and sodium salicylate.

Examples of the steroidal anti-inflammatory agents include hydrocortisone, prednisolone, fluocinolone acetonide, fludroxycortide, methyl prednisolone, hydrocortisone acetate, triamcinolone acetonide, dexamethasone, betamethasone acetate, diflucortolone velerate, clobetasol propionate and fluocinonide.

Examples of the vasodilators include diltiazem, verapamil, pentaerythritol tetra-nitrate, dipyridamole, isosorbide nitrate, nifedipine, nicotinic acid and norepinephrine.

Examples of the antihypertensive and antiarrhythmic agents include propranolol, atenolol, pindolol, kinidine sulfate, ajimaline, alprenolol hydrochloride, metoprolol tartrate, nadolol, timolol maleate and disopyramide.

Examples of the hypotensive agent include clonidine hydrochloride, captopril, prazosin hydrochloride, penbutolol sulphate, guanabenz acetate, guanfacine hydrochloride, bunazosin hydrochloride, enalapril maleate, alotinolol hydrochloride, bunitrolol hydrochloride and guanethidine sulfate.

Examples of the antitussive expectorants include procaterol hydrochloride, terbutaline sulfate, fenoterol hydrobromide, tulobuterol hydrochloride, ambroxol hydrochloride, pirbuterol hydrochloride, mabuterol hydrochloride, clenbuterol hydrochloride, trimetoquinol hydrochloride and formoterol fumarate.

Illustrative of the antineoplastics include glycolpyrronium bromide, vincristin sulfate, vinblastin sulfate and fluorouracil.

Examples of the local anesthetics include benzocaine, procaine, lidocaine, tetracaine, bupivacaine and mepivacaine.

Examples of the hormone preparations include steroidal hormone preparations such as estrogen, estradiol, testosterone, progesterone and prostaglandin; adrenocortical hormone preparations such as hydrocortisone sodium succinate, methylprednisolone sodium succinate, cortisone acetate, triamcinolone diacetate, dexamethasone, hydrocortisone, prednisolone, methylprednisolone, dexamethasone sodium phosphate and hydrocortisone sodium phosphate; and peptide hormone preparations such as insulin.

Examples of the antiasthmatic and antiallergic agents include ketotifen fumarate, azelastine hydrochloride, sodium cromoglycate, emedastine difumarate, tranilast and ciclosporin.

Examples of the antihistaminics include cycloheptadine hydrochloride, diphenhydramine hydrochloride, phenbenzamine, mequitazine and chlorpheniramine maleate.

Examples of the anticoagulants include heparin, urokinase and tPA and those of antispasmodics include scopolamine, clofluperrole, N-methylscopolamine methylsulfate and papaverine hydrochloride.

Examples of the cerebral circulation and metabolism improvers include vinpocetine, flunarizine hydrochloride, nicardipine hydrochloride, brovincamine fumarate, dihydroergotoxine mesylate, ifenprodil tartrate, isoxsuprine hydrochloride, diltiazem hydrochloride and etidronate disodium.

Examples of antidepressant and antianxiety agents include maprotiline hydrochloride, etizolam, diazepam, bromazepam, amitriptyline hydrochloride, mianserin hydrochloride, chlorpromazine, spiperone and imipramine hydrochloride.

Examples of the vitamin D preparations include alfacalcidol and ergocalciferol.

Examples of the hypoglycemic agents include glibenclamide and gliclazide.

Examples of the antiulcer agents include clebopride malate, famotidine and glycopyrronium bromide.

Examples of the hypnotics include phenobarbital and amobarbital.

Examples of the antibiotics include tetracycline, chloramphenicol, phenoxymethylpenicillin potassium and erythromycin.

Examples of the antifungal agents include ciclopirox olamine and amphotericin B.

Examples of the sedative agents include scopolamine hydrobromide, morphine hydrochloride and fentanyl citrate.

Examples of the bronchodilator agents include theophylline, formoterol fumarate, salbutamol sulfate, terbutaline sulfate and ephedrine hydrochloride.

Examples of the antiviral agents include vidarabine and idoxuridine.

Examples of the dysuric agents include oxybutynin hydrochloride, arginine-vasopressin and desmopressin acetate.

When an adhesive base material containing such a medicament is prepared, it can be prepared by dissolving or suspending the medicament in an aqueous solution of polyvinyl alcohol, adding a hydrophilic crosslinked polymer to the resulting solution or suspension, spreading the mixture between silicone sheets and subjecting to the freeze-thaw method or alternatively by preparing a gel, to which a medicament has not been added, by the freeze-thaw method and then immersing it in a solution of the medicament.

Although the amount of the medicament to be dissolved or suspended in the aqueous solution of polyvinyl alcohol differs with its clinically-required amount and a single dosage, preferred is 0.1 to 10 wt. % (w/w%) to the aqueous solution. It is also possible to add at need one or more ingredients usually employed for a dermatologic medicine, such as a skin irritant, percutaneous absorption enhancer, stabilizer, aging resistant, sunscreening agent and/or antioxidant. In addition, the pH of the dermatologic medicine can be adjusted with an acid or alkali.

The adhesive base material containing a medicament therein can be used as pads for iontophoresis or phonophoresis as well as usual plasters.

EXAMPLES

The present invention will hereinafter be described more specifically by the following examples. It should however be borne in mind that this invention is by no means limited to or by the examples.

PREPARATION EXAMPLE 1

(Preparation of a GEMA-MMA-bis copolymer)

2-Glucosyloxyethyl methacrylate (hereinafter abbreviated as "GEMA") and methyl methacrylate (hereinafter abbreviated as "MMA") were mixed at varied molar ratios of from 10:0.1 to 10:1. To each of the resulting mixed monomers, N,N'-methylenebisacrylamide (hereinafter abbreviated as "bis") was added as a crosslinker at a molar ratio of 800:1. To the resulting monomer mixtures, added was 2,2'-azobis(2-amidinopropane)dihydrochloride (hereinafter abbreviated as "V50") in an amount of 0.5 wt. % based on the entirety of the resulting monomer mixture. After nitrogen purging and degassing, the resulting mixture was subjected to polymerization reaction at 65° C. for 17 hours.

After the completion of the polymerization reaction, a series of procedures, that is, swelling with water, washing with isopropyl alcohol, vacuum drying and pulverization, was repeated twice to purify the resulting polymer. The polymer so purified was sifted through an 80-mesh sieve, whereby the hydrophilic crosslinked polymer was obtained in the form of fine powder.

PREPARATION EXAMPLE 2

(Preparation of a GEMA-MMA-bis copolymer in the form of a plate)

Between two slide glasses with a 0.5 mm-thick spacer interposed therebetween, polymerization reaction was conducted as in Preparation Example 1.

After the completion of the polymerization reaction, a series of the procedures, that is, swelling with water, washing with isopropyl alcohol and vacuum drying, was repeated twice to conduct purification, whereby a hydrophilic crosslinked polymer were obtained in the form of a plate.

PREPARATION EXAMPLE 3

(Preparation of a GEMA-MMA-bis copolymer)

To a 10:5 (molar ratio) mixed monomer of GEMA and MMA, bis was added as a crosslinker at varied molar ratios of from 100:1 to 3200:1. Polymerization reaction and purification operation were conducted in a similar manner to Preparation Example 1, whereby hydrophilic crosslinked polymers were obtained in the form of fine powder.

PREPARATION EXAMPLE 4

(Preparation of a GEMA-MMA-bis copolymer in the form of a plate)

Between two slide glasses with a 0.5 mm-thick spacer interposed therebetween, the monomer mixture and the crosslinker which were the same as those employed in Preparation Example 3 were added and polymerization reaction and purification operation were conducted as in Preparation Example 2, whereby a hydrophilic crosslinked polymer was obtained in the form of a plate.

PREPARATION EXAMPLE 5

(Preparation of a GEMA-BA-bis copolymer)

GEMA and n-butyl acrylate (hereinafter abbreviated as "BA") were mixed at varied molar ratios of 10:0.1 to 10:1. To each of the resulting monomer mixture, bis was added as a crosslinker at a molar ratio of 800:1. Polymerization reaction and purification operation were conducted in a similar manner to Preparation Example 1, whereby a hydrophilic crosslinked polymer was obtained in the form of fine powder.

PREPARATION EXAMPLE 6

(Preparation of a GEMA-BA-bis copolymer in the form of a plate)

Between two slide glasses with a 0.5 mm-thick spacer interposed therebetween, the monomer mixture and the crosslinker which were the same as those employed in Preparation Example 5 were added and polymerization reaction and purification operation were conducted as in Preparation Example 2, whereby a hydrophilic crosslinked polymer was obtained in the form of a plate.

PREPARATION EXAMPLE 7
(Preparation of a GEMA-HEMA-bis copolymer)

GEMA and 2-hydroxyethyl methacrylate (hereinafter abbreviated as "HEMA") were mixed at varied molar ratios of 10:0.1 to 10:1. To each of the resulting monomer mixtures, bis was added as a crosslinker at a molar ratio of 800:1. Polymerization reaction and purification operation were conducted in a similar manner to Preparation Example 1, whereby hydrophilic crosslinked polymers were obtained in the form of fine powder.

PREPARATION EXAMPLE 8
(Preparation of a GEMA-HEMA-bis copolymer in the form of a plate)

Between two slide glasses with a 0.5 mm-thick spacer interposed therebetween, the monomer mixture and the crosslinker which were the same as those employed in Preparation Example 7 were added and polymerization reaction and purification operation were conducted as in Preparation Example 2, whereby a hydrophilic crosslinked polymer was obtained in the form of a plate.

Out of the hydrophilic crosslinked polymers obtained in the above Preparation Examples, Gels 1–19 shown in Table 1 were employed in the following examples. In Table 1, the concentration of each monomer is indicated as mole% based on the entirety of the resulting monomer mixture. In addition, a swelling rate of each gel is also shown.

TABLE 1

| Gel | Copolymer | Swelling rate |
|---|---|---|
| Gel 1 | GEMA-MMA-bis (MMA concentration: 16.7 mole %, bis concentration: 0.125 mole %) | 658 |
| Gel 2 | GEMA-MMA-bis (MMA concentration: 4.8 mole %, bis concentration: 0.125 mole %) | 754 |
| Gel 3 | GEMA-MMA-bis (MMA concentration: 9.1 mole %, bis concentration: 0.125 mole %) | 717 |
| Gel 4 | GEMA-MMA-bis (MMA concentration: 16.7 mole %, bis concentration: 0.125 mole %) | 658 |
| Gel 5 | GEMA-MMA-bis (MMA concentration: 33.3 mole %, bis concentration: 0.125 mole %) | 461 |
| Gel 6 | GEMA-MMA-bis (MMA concentration: 50 mole %, bis concentration: 0.125 mole %) | 370 |
| Gel 7 | GEMA-MMA-bis (MMA concentration: 16.7 mole %, bis concentration: 0.03125 mole %) | 622 |
| Gel 8 | GEMA-MMA-bis (MMA concentration: 16.7 mole %, bis concentration: 0.0625 mole %) | 630 |
| Gel 9 | GEMA-MMA-bis (MMA concentration: 16.7 mole %, bis concentration: 0.125 mole %) | 607 |
| Gel 10 | GEMA-MMA-bis (MMA concentration: 16.7 mole %, bis concentration: 0.25 mole %) | 626 |
| Gel 11 | GEMA-MMA-bis (MMA concentration: 16.7 mole %, bis concentration: 0.5 mole %) | 624 |
| Gel 12 | GEMA-MMA-bis (MMA concentration: 16.7 mole %, bis concentration: 1 mole %) | 568 |
| Gel 13 | GEMA-BA-bis (BA concentration: 4.8 mole %, bis concentration: 0.125 mole %) | 932 |
| Gel 14 | GEMA-BA-bis (BA concentration: 4.8 mole %, bis concentration: 0.125 mole %) | 932 |
| Gel 15 | GEMA-BA-bis (BA concentration: 9.1 mole %, bis concentration: 0.125 mole %) | 843 |
| Gel 16 | GEMA-BA-bis (BA concentration: 16.7 mole %, bis concentration: 0.125 mole %) | 813 |
| Gel 17 | GEMA-BA-bis (BA concentration: 33.3 mole %, bis concentration: 0.125 mole %) | 819 |
| Gel 18 | GEMA-BA-bis (BA concentration: 50 mole %, bis concentration: 0.125 mole %) | 806 |
| Gel 19 | GEMA-HEMA-bis (HEMA concentration: 4.8 mole %, bis concentration: 0.125 mole %) | 820 |

EXAMPLE 1

Polyvinyl alcohol having an average polymerization degree of 2000 and a saponification degree of 98±0.5 mole% (which polyvinyl alcohol will hereinafter be abbreviated as "PVA2000") and sodium azide were mixed uniformly at a ratio described in Formulation 1 shown in Table 2. The resulting mixture was then charged gradually in purified water which had been heated to 55°–75° C., followed by stirring, whereby a uniform solution was obtained.

With portions of the resulting solution, Gel 1 was mixed in an amount of 0, 10, 12.5, 16.7 and 25 wt. %, respectively. Each (0.4 g) of the resulting mixtures was caused to spread uniformly to an area of 2 cm×2 cm between silicone sheets with 0.5 mm spacer interposed therebetween. It was freezed at −20° C. and then allowed to stand at room temperature (which procedure will hereinafter be called "freeze-thaw") and this freeze-thaw procedure was repeated twice overnight, whereby a pad was produced. In this manner, various pads were produced.

TABLE 2

| (Formulation 1) | |
|---|---|
| PVA2000 | 5 g |
| Sodium azide | 0.1 g |
| Purified water | 100 g in total |

EXAMPLE 2

In a similar manner to Example 1 except that 5 g of PVA2000 were replaced by 3, 4, 5, 6 and 7 g of polyvinyl alcohol having an average polymerization degree of 2400 and a saponification degree of 98±0.5 mole% (which polyvinyl alcohol will hereinafter be abbreviated as "PVA2400"), PVA solutions were prepared, respectively. To the resulting solutions, Gel 1 was added in an amount of 16.7%, respectively. The resulting mixtures were treated in a similar manner to Example 1, whereby pads were produced.

EXAMPLE 3

In a similar manner to Example 1 except that PVA2000 was replaced by polyvinyl alcohol having an average polymerization degree of 1700 and a saponification degree of 98±0.5 mole% (which polyvinyl alcohol will hereinafter be abbreviated as "PVA1700"), a PVA solution was prepared.

To the resulting solution, Gel 1 was added in an amount of 16.7%. The resulting mixture was treated in a similar manner to Example 1, whereby a pad was produced.

EXAMPLE 4

In a similar manner to Example 1, a PVA solution of Formulation 1 was prepared. Portions of the resulting solution were mixed with Gels 2, 3, 4, 5 and 6 in an amount of 16.7%, respectively. The resulting mixtures were treated in a similar manner to Example 1, whereby pads were produced.

EXAMPLE 5

In a similar manner to Example 1, a PVA solution of Formulation 1 was prepared. Portions of the resulting solution were mixed with Gels 7, 8, 9, 10, 11 and 12 in an amount of 16.7%, respectively. The resulting mixtures were treated in a similar manner to Example 1, whereby pads were produced.

EXAMPLE 6

The freeze-thaw was repeated twice at the thawing temperatures of 5° C. and 25° C., respectively. In a similar manner to Example 1, pads were produced.

EXAMPLE 7

Using sodium hyaluronate (hereinafter abbreviated as "HA") in amounts of 0, 0.25, 0.5 and 1 g, PVA solutions were prepared in a similar manner to Example 1, respectively. With the resulting solutions, Gel 1 was mixed in a proportion of 16.7%. The resulting mixtures were treated in a similar manner to Example 1, whereby pads were produced.

EXAMPLE 8

In a similar manner to Example 1 except that Gel 1 was replaced by Gel 13 and Gel 19, pads were produced, respectively.

EXAMPLE 9

A PVA solution of Formulation 1 was prepared in a similar manner to Example 1. With portions of the resulting solution, Gels 14, 15, 16, 17 and 18 were mixed in a proportion of 16.7%, respectively. The resulting mixtures were treated in a similar manner to Example 1, whereby pads were produced.

EXAMPLE 10

In a similar manner to Example 7 except that Gel 1 was replaced by Gel 13 and Gel 19, pads were produced, respectively.

Test 1

Adhesion and forming property of the pads obtained in the above Examples were evaluated.

(Evaluation Method)
(1) Adhesion

Figure 1B:
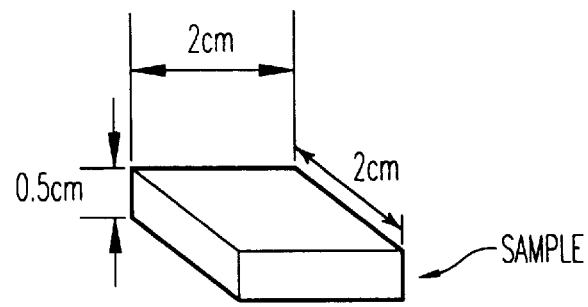

Using an apparatus of the construction illustrated in FIG. 1, the 2 cm×2 cm pads obtained in the above examples were each peeled off from glass at a fixed rate of 2 cm/min and the load at the time of the peeling was measured.
(2) Forming property (mechanical strength)

An operation of adhering a pad to a brachial bent part of human body and peeling the pad therefrom was repeated twice and the forming property was evaluated.

(Results)

Figure 2:
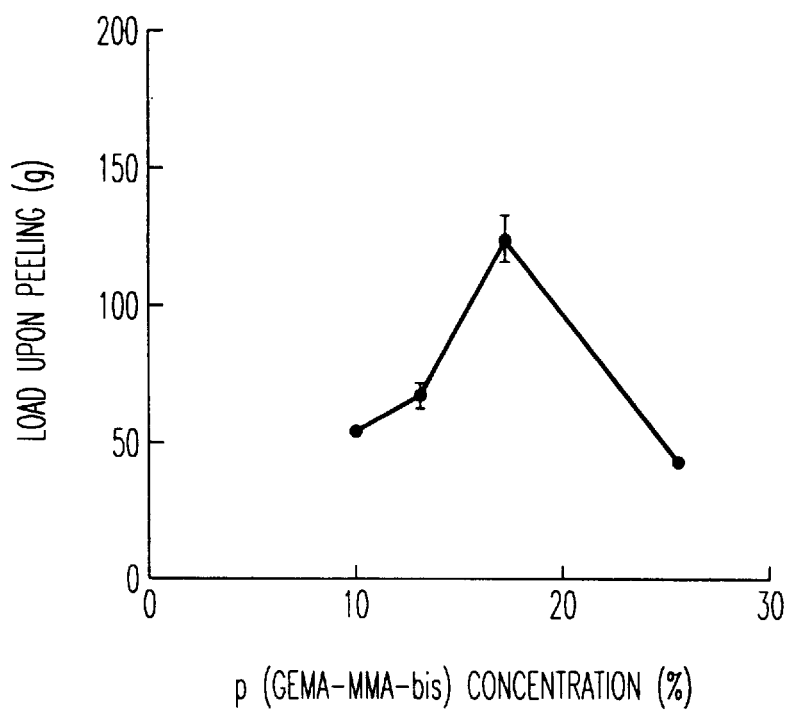
FIG. 2 diagrammatically illustrates a comparison in adhesion with varied concentrations of a p(GEMA-MMA-bis) copolymer.

(1) In FIG. 2, a comparison in adhesion among the pads obtained in Example 1 at varied concentrations of a p(GEMA-MMA-bis) copolymer was depicted.

It was found that with an increase in the concentration, adhesion was eminently improved, showing the maximum at the concentration of 16.7%.

It was also found that each pad showed almost no change in its form at the time of peeling so that it could be adhered or peeled off.

Figure 3:
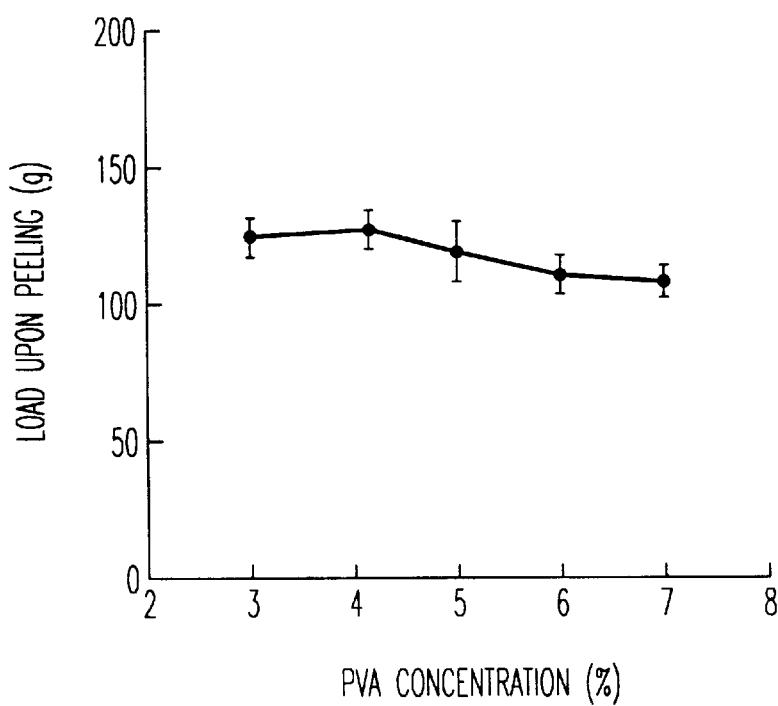
FIG. 3 diagrammatically illustrates a comparison in adhesion with varied concentrations of PVA.

(2) In FIG. 3, a comparison in adhesion among the pads obtained in Example 2 at varied concentrations of PVA was depicted.

It was found that there was almost no change in adhesion in spite of the change in the PVA concentration.

It was also found that each pad showed almost no change in its form at the time of peeling so that it could be adhered or peeled off.

Figure 4:
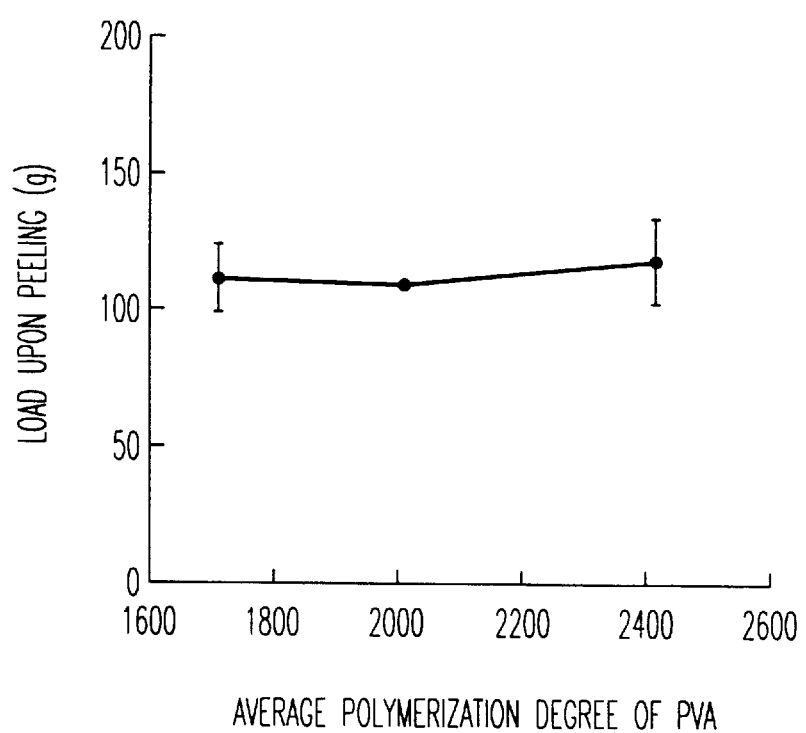
FIG. 4 diagrammatically illustrates a comparison in adhesion with varied average polymerization degrees of PVA.

(3) In FIG. 4, a comparison in adhesion among the pads obtained in Examples 1–3 and having different average polymerization degrees was depicted.

It was found that there was almost no change in adhesion in spite of the difference in the average polymerization degree.

It was also found that each pad showed almost no change in its form at the time of peeling so that it could be adhered or peeled off.

Figure 5:
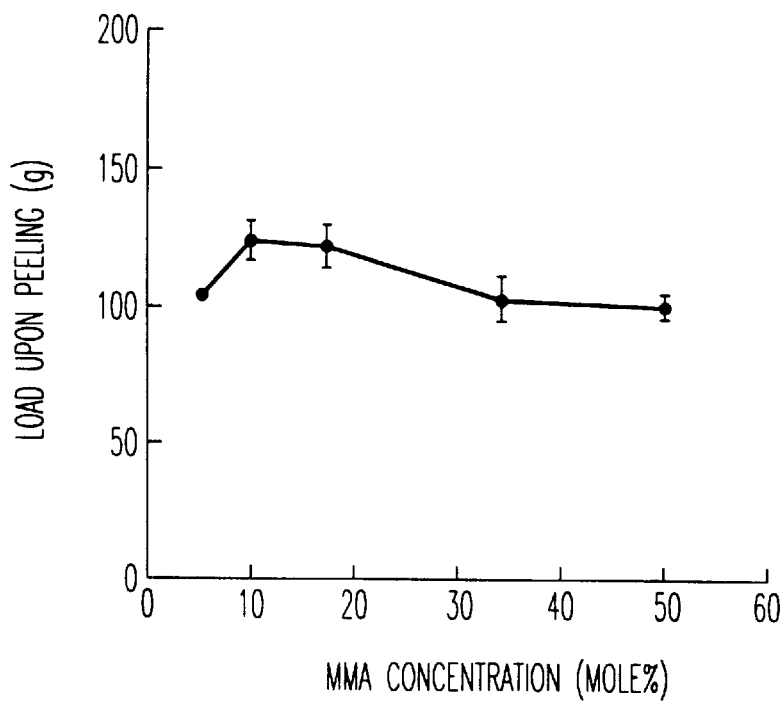
FIG. 5 diagrammatically illustrates a comparison in adhesion with varied MMA concentrations of a p(GEMA-MMA-bis) copolymer.

(4) In FIG. 5, a comparison in adhesion among the pads obtained in Example 4 at varied MMA concentrations of a p(GEMA-MMA-bis) copolymer was depicted.

It was found that there was no change in adhesion when the MMA concentration was 33.3 mole% or higher.

It was also found that each pad showed almost no change in its form at the time of peeling so that it could be adhered or peeled off.

Figure 6:
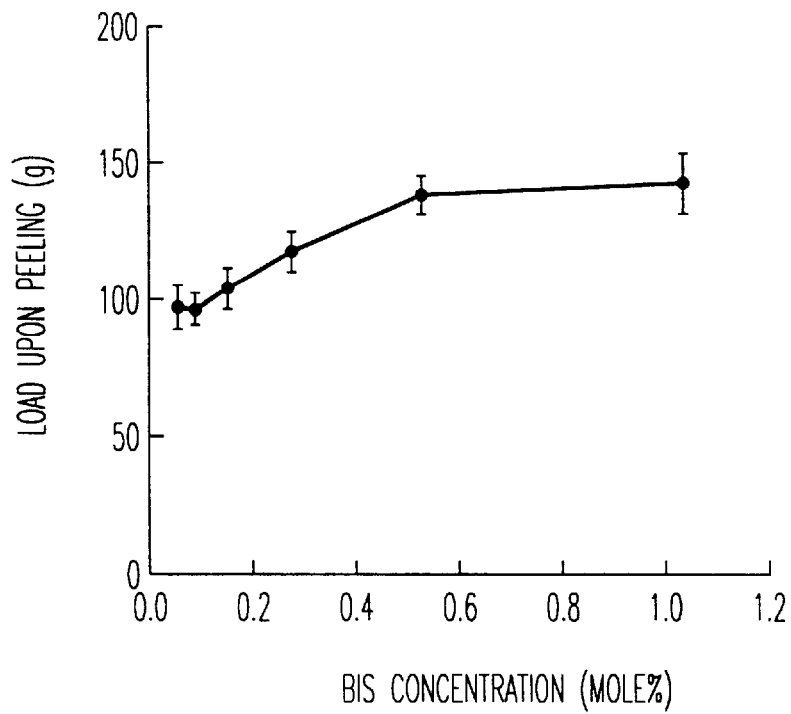
FIG. 6 diagrammatically illustrates a comparison in adhesion with varied bis concentrations of a g(GEMA-MMA-bis) copolymer.

(5) In FIG. 6, a comparison in adhesion among the pads obtained in Example 5 at varied bis concentrations of a p(GEMA-MMA-bis) copolymer was depicted.

It was found that with an increase in the bis concentration, adhesion showed an improvement.

It was also found that each pad showed almost no change in its form at the time of peeling so that it could be adhered or peeled off.

Figure 7:
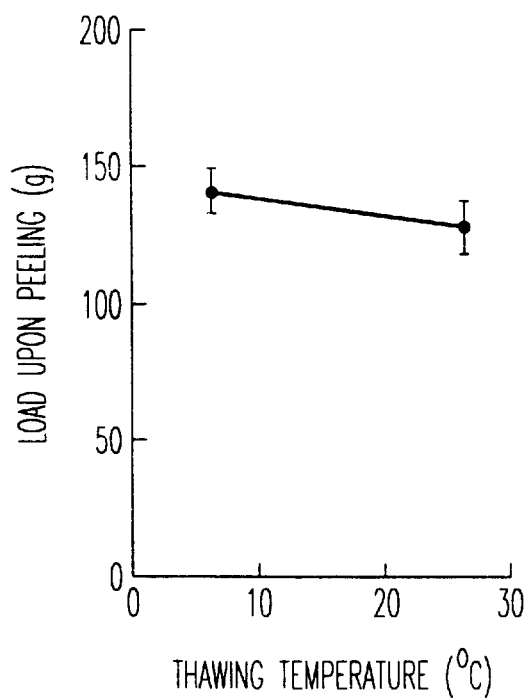
FIG. 7 diagrammatically illustrates a comparison in adhesion with varied thawing temperatures, FIG. 8 diagrammatically illustrates a comparison in adhesion with varied HA concentrations.

(6) In FIG. 7, a comparison in adhesion among the pads obtained in Example 6 at varied thawing temperatures was depicted.

It was found that there was almost no change in adhesion.

It was also found that each pad showed almost no change in its form at the time of peeling so that it could be adhered or peeled off.

Figure 8:
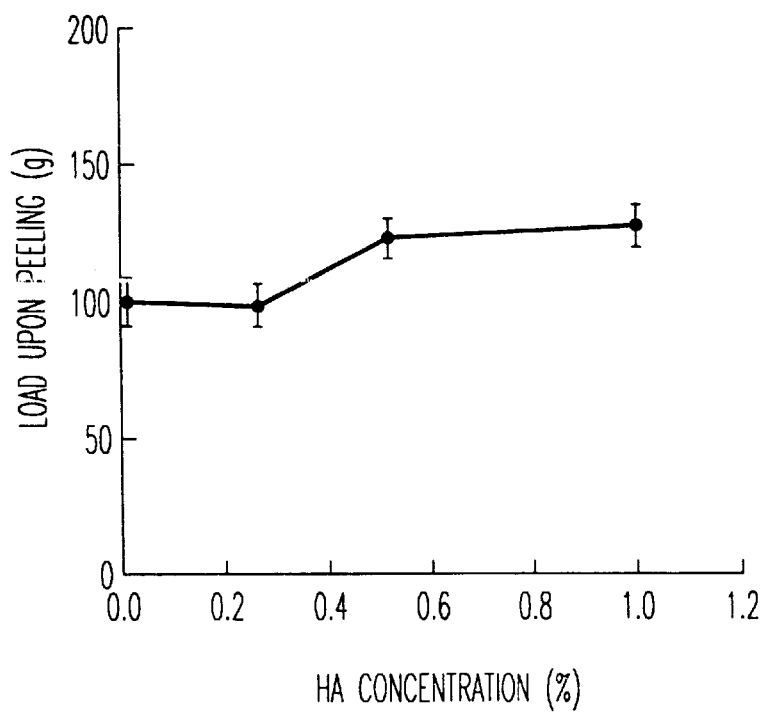

(7) In FIG. 8, a comparison in adhesion among the pads obtained in Example 7 at varied hydrophilic polymer (HA) concentrations was depicted.

It was found that when HA was added, with an increase in the concentration, adhesion tended to show an improvement.

It was also found that each pad showed almost no change in its form at the time of peeling so that it could be adhered or peeled off.

Figure 9:
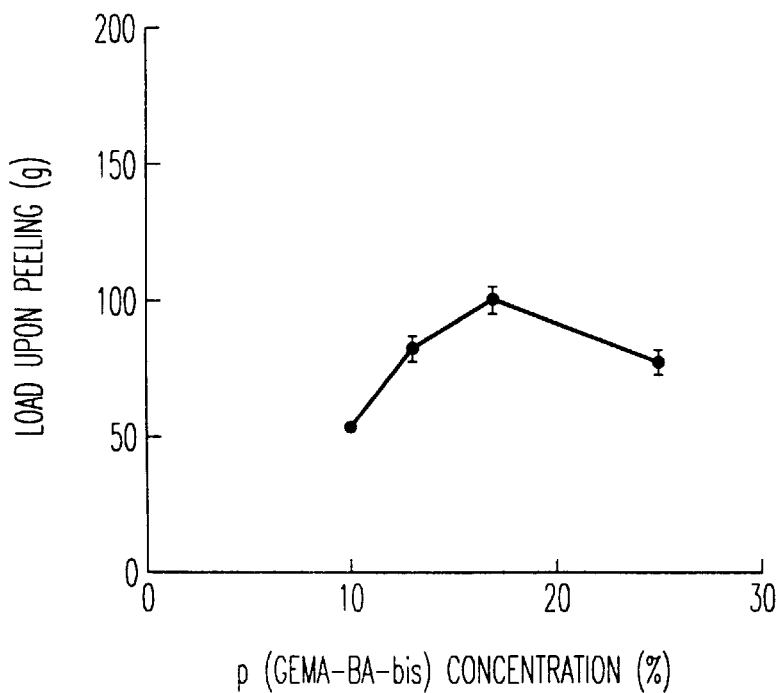
FIG. 9 diagrammatically illustrates a comparison in adhesion with varied concentrations of a p(GEMA-BA-bis) copolymer.
Figure 10:
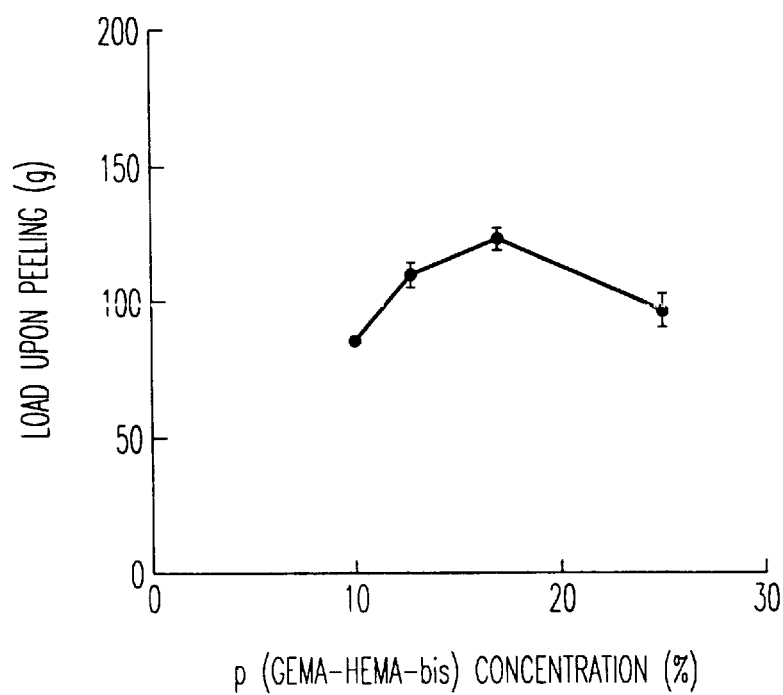
FIG. 10 diagrammatically illustrates a comparison in adhesion with varied concentrations of a p(GEMA-HEMA-bis) copolymer.

(8) In FIGS. 9 and 10, comparisons in adhesion among the pads obtained in Example 8 at varied concentrations of p(GEMA-BA-bis) and p(GEMA-HEMA-bis) copolymers were depicted, respectively.

It was found that in either case, with an increase in the concentration, the adhesion was eminently improved, showing the maximum at the concentration of 16.7 mole%.

It was also found that each pad showed almost no change in its form at the time of peeling so that it could be adhered or peeled off.

Figure 11:
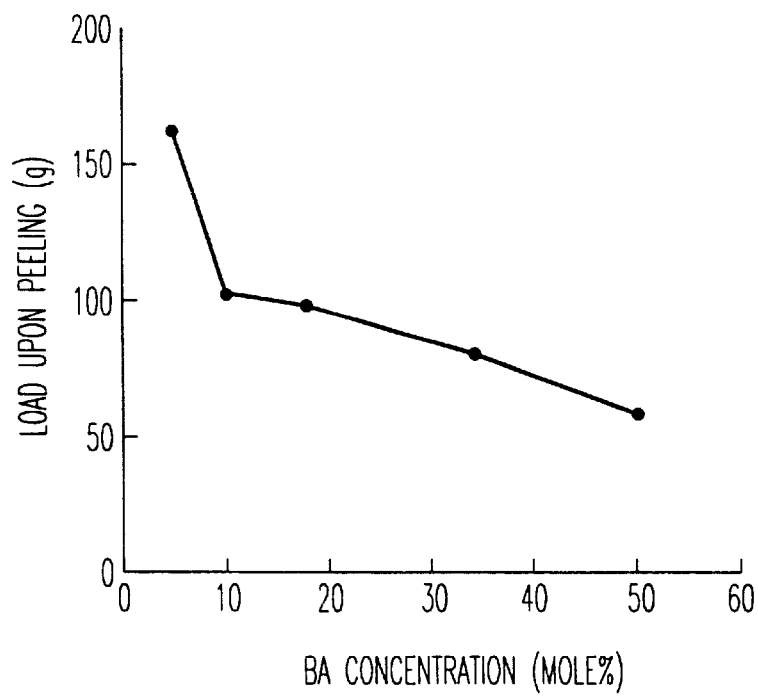
FIG. 11 diagrammatically illustrates a comparison in adhesion with varied BA concentrations of a p(GEMA-BA-bis) copolymer.

(9) In FIG. 11, a comparison in adhesion among the pads obtained in Example 9 at varied BA concentrations of a p(GEMA-BA-bis) copolymer was depicted.

It was found that with an increase in the concentration, adhesion showed a lowering tendency.

It was also found that each pad showed almost no change in its form at the time of peeling so that it could be adhered or peeled off.

Figure 12:
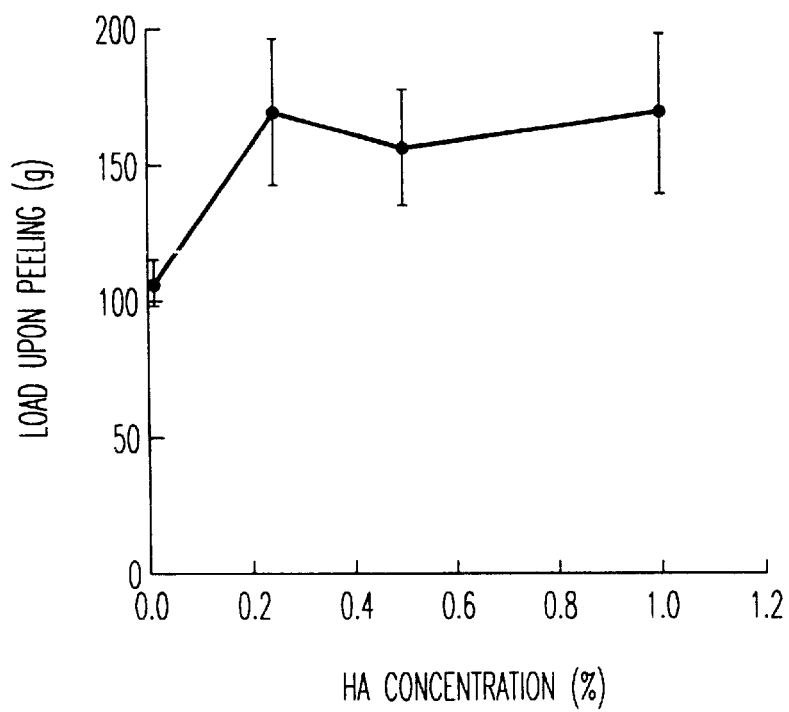
FIG. 12 diagrammatically illustrates a comparison in adhesion with varied HA concentrations.
Figure 13:
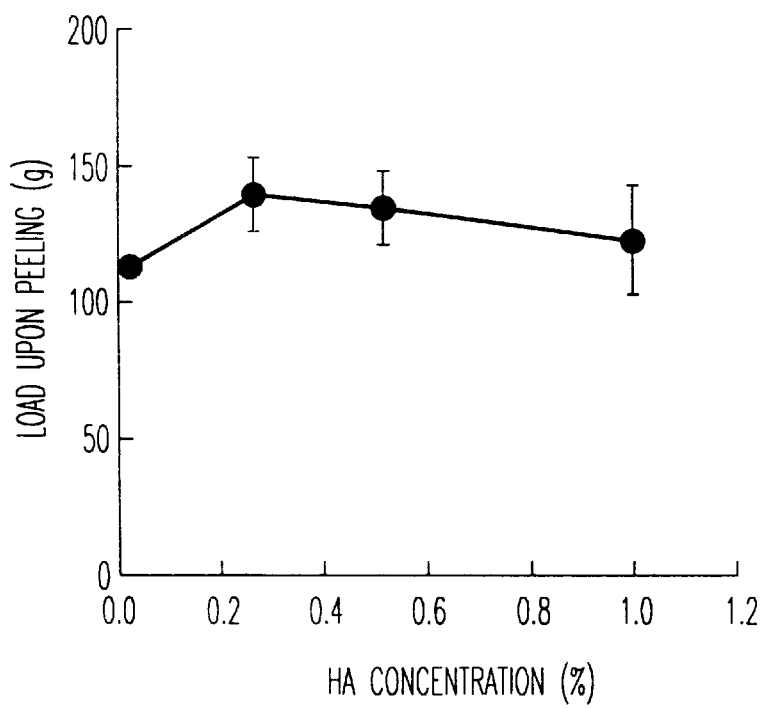
FIG. 13 diagrammatically illustrates another comparison in adhesion with varied HA concentrations.

(10) In FIGS. 12 and 13, comparisons in adhesion among the pads obtained in Example 10 at varied hydrophilic polymer (HA) concentrations of p(GEMA-BA-bis) and p(GEMA-HEMA-bis) copolymers were depicted, respectively.

It was found that when HA was added, with an increase in its concentration, adhesion showed an increasing tendency.

It was also found that each pad showed almost no change in its form at the time of peeling so that it could be adhered or peeled off.

Test 2

Water retention properties of the pads obtained in Example 1 was evaluated. The results are shown in Table 3.

(Evaluation method)

A pad was placed on a plastic Petri dish and was allowed to stand in a thermostatic chamber of 37° C. Upon elapsed times of 0, 1, 3 and 5 hours after that, the pad was taken out from the Petri dish and its weight was measured. In accordance with the following formula, the weight change rate was determined.

TABLE 3

| Polymer concentration (%) | 0 | 1 hour | 3 hours | 5 hours |
|---|---|---|---|---|
| 0 | 0 | 39.9 | 85.4 | 94.7 |
|   | (100) | (60.1) | (14.6) | (5.3) |
| 25 | 0 | 34.4 | 65.6 | 68.2 |
|   | (100) | (65.6) | (34.4) | (31.8) |

*Upper numerals indicate a weight change rate calculated in accordance with the above formula.
Numerals in parenthesis indicate a water content.

Weight change rate (%) = $\dfrac{W_o - W}{W_o}$ × 100

$W_o$ = Initial weight
$W$ = Weight upon measurement

Figure 14:
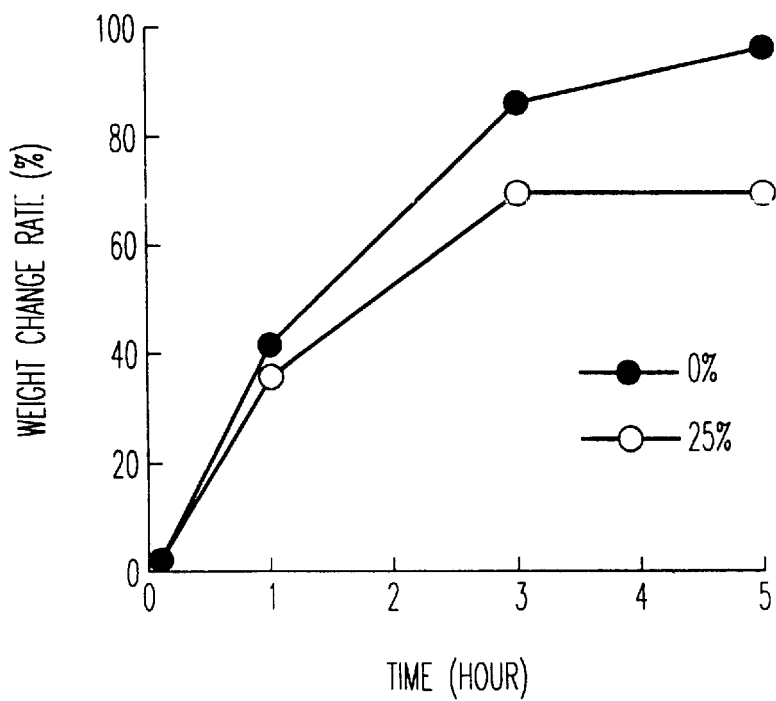
FIG. 14 diagrammatically illustrates a weight change ratio of a pad to be obtained in Example 1.

In FIG. 14, a comparison in the weight change rate was depicted. It was found that the addition of a polymer (hydrophilic crosslinked polymer) lowered the weight change rate, in other words, heightened the water retention effects.

What is claimed is:

1. A hydrophilic adhesive base material comprising the following components (A) and (B):

(A) a hydrophilic crosslinked polymer obtained by polymerizing:

(a) a glucosyloxyalkyl (meth)acrylate, (b) an alkyl (meth)acrylate and/or a hydroxyalkyl (meth)acrylate, and (c) a polyfunctional monomer; and (B) polyvinyl alcohol, obtained by freezing an aqueous solution containing said component (A) and from 3 to 10 wt. % of said component (B), and then thawing the freezed solution.

2. A hydrophilic adhesive base material according to claim 1, wherein in the hydrophilic crosslinked polymer (A), a molar ratio of the component (a) and the component (b) falls within a range of from 10:0.1 to 10:1.

3. A hydrophilic adhesive base material according to claim 1 or 2, wherein in the hydrophilic crosslinked polymer (A), a molar ratio of the component (c) and the sum of the component (a) and the component (b) falls within a range of from 1:100 to 1:3200.

4. A hydrophilic adhesive base material according to claim 1, which comprises 15–50 wt. % (w/w%) of the hydrophilic crosslinked polymer (A).

5. A hydrophilic adhesive base material according to claim 1, wherein the polyvinyl alcohol (B) has a saponification degree of at least 95 mole%.

6. A hydrophilic adhesive base material according to claim 1, wherein the polyvinyl alcohol (B) has an average polymerization degree of at least 1,700.

7. A hydrophilic adhesive base material according to claim 1, which has peel strength of at least 20 g/cm$^2$ when measured relative to glass.

8. A process for the preparation of a hydrophilic adhesive base material, which comprises freezing an aqueous solution containing the following components (A) and (B):

(A) a hydrophilic crosslinked polymer obtained by polymerizing:

(a) a glucosyloxyalkyl (meth)acrylate, (b) an alkyl (meth)acrylate and/or a hydroxyalkyl (meth)acrylate, and (c) a polyfunctional monomer; and (B) polyvinyl alcohol, and then thawing the freezed solution.

9. A dermatologic medicine composition comprising a hydrophilic adhesive base material according to claim 1 and a medicament.

10. A dermatologic medicine composition according to claim 9, wherein the medicament is any one of a protein and peptide preparation, an antipyretic, antiphlogistic and analgesic agent, a steroidal anti-inflammatory agent, a vasodilator, an antihypertensive and antiarrhythmic agent, a hypotensive agent, an antitussive expectorant, an antineoplastic, a local anesthetic, a hormone preparation, an antiasthmatic and antiallergic agent, an antihistaminic, an anticoagulant, an antispasmodic, a cerebral circulation and metabolism improver, an antidepressant and antianxiety agent, a vitamin D preparation, a hypoglycemic agent, an antiulcer agent, a hypnotic, an antibiotic, an antifungal agent, a sedative agent, a bronchodilator agent, an antiviral agent and a dysuric agent.

* * * * *

UNITED STATES PATENT AND TRADEMARK OFFICE
CERTIFICATE OF CORRECTION

PATENT NO. : 5,773,028
DATED : June 30, 1998
INVENTOR(S) : Toshio INAGI et al

It is certified that error appears in the above-identified patent and that said Letters Patent is hereby corrected as shown below:

Column 16, line 9, "10:0.1 to 10:1" should read --10:0.1 to 10:10--.

Signed and Sealed this

Eighth Day of December, 1998

Attest:

BRUCE LEHMAN

Attesting Officer

Commissioner of Patents and Trademarks